United States Patent
Yong

(10) Patent No.: US 11,883,629 B2
(45) Date of Patent: Jan. 30, 2024

(54) SENSOR FOR DETECTING TISSUE INFILTRATION

(71) Applicant: Becton, Dickinson and Company, Franklin Lakes, NJ (US)

(72) Inventor: Zhee Min Jimmy Yong, Telok Kurau (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 535 days.

(21) Appl. No.: 17/063,228

(22) Filed: Oct. 5, 2020

(65) Prior Publication Data

US 2021/0106754 A1 Apr. 15, 2021

Related U.S. Application Data

(60) Provisional application No. 62/914,874, filed on Oct. 14, 2019.

(51) Int. Cl.
*A61M 5/168* (2006.01)
*A61M 25/06* (2006.01)

(52) U.S. Cl.
CPC .... *A61M 5/16836* (2013.01); *A61M 25/0606* (2013.01); *A61M 2205/3306* (2013.01); *A61M 2205/6081* (2013.01)

(58) Field of Classification Search
CPC .......... A61M 5/16836; A61M 25/0606; A61M 2205/3306; A61M 2205/6081; A61B 2562/0261; A61B 5/4878; A61B 5/68335; A61B 5/1077; A61B 5/02042; A61F 2013/0094; A61F 2013/00429
See application file for complete search history.

(56) References Cited

U.S. PATENT DOCUMENTS

| | | | | |
|---|---|---|---|---|
| 4,213,463 | A | * 7/1980 | Osenkarski | A61B 5/061 607/152 |
| 6,432,074 | B1 | 8/2002 | Ager et al. | |
| 2008/0264327 | A1 | 10/2008 | Pett et al. | |
| 2018/0280612 | A1* | 10/2018 | Krupnick | A61M 5/158 |

FOREIGN PATENT DOCUMENTS

| | | |
|---|---|---|
| WO | 2018/0187027 | 10/2018 |
| WO | 2019/0136559 | 7/2019 |

* cited by examiner

*Primary Examiner* — Lauren P Farrar
*Assistant Examiner* — Hamza A Darb
(74) *Attorney, Agent, or Firm* — Kirton McConkie; Whitney Blair; Kevin Stinger

(57) ABSTRACT

A sensor for detecting infiltration at a catheter infusion site may include a first elongate sensor member couplable to a first location proximate the catheter infusion site, and a second elongate sensor member couplable to a second location proximate the catheter infusion site. The first elongate sensor member may include a first marking and the second elongate sensor member may include a second marking. The first elongate sensor member may slidably couple with and translate relative to the second elongate sensor. The first and second markings may indicate a range of relative positions between the first and second elongate sensor members as the first and second elongate sensor members translate relative to each other. At least one relative position within a range of relative positions between the first and second elongate sensor members may be indicative of infiltration at the catheter infusion site.

14 Claims, 4 Drawing Sheets

SENSOR FOR DETECTING TISSUE INFILTRATION

RELATED APPLICATIONS

This application claims the benefit of U.S. Provisional Application No. 62/914,874, filed Oct. 14, 2019, and entitled SENSOR FOR DETECTING TISSUE INFILTRATION which is incorporated herein in its entirety.

BACKGROUND

Catheters are commonly used for a variety of infusion therapies. For example, catheters may be used for infusing fluids into a patient such as saline solution, medication, total parenteral nutrition, etc. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and the introducer needle are typically inserted at a shallow angle through the skin and into a blood vessel of the patient, such as an artery, a vein, or any other vasculature of the patient. Once the PIVC has been properly placed within the blood vessel, the introducer needle may be withdrawn and the PIVC may be secured within the blood vessel by securing a catheter adapter (coupled with the PIVC) to the skin of the patient with dressing. Other common types of catheters include, but are not limited to, peripherally inserted central catheters ("PICC"), central venous catheters ("CVC"), etc.

Unfortunately, fluids delivered to the patient via catheter can sometimes leak into tissues surrounding a catheter infusion site. Infiltration of fluid into these tissues may be caused by: (1) poor initial placement of the catheter; (2) subsequent dislodgement of the catheter from within a blood vessel; (3) extravasation of catheter fluids from a blood vessel into surrounding tissues, etc.

Accordingly, improved sensors and methods for detecting fluid infiltration at a catheter infusion site would be desirable. For example, improved sensors and methods for detecting fluid infiltration may help a clinician quickly identify when an infiltration event has occurred. The clinician can then take immediate corrective action to treat the infiltration event, such as: (1) preventing further infiltration from occurring; (2) elevating the infiltration site to help reduce swelling; (3) applying a warm or cold compress (depending on the fluid) to the infiltration site to help reduce swelling and/or discomfort; (4) treating the patient with any appropriate medication(s) that may be required, etc.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to sensors and methods for detecting fluid infiltration at a catheter infusion site of a patient. The various sensors and methods of the present disclosure have been developed in response to the present state of the art, and in particular, in response to the problems and needs in the art that have not yet been fully solved by currently available sensors and methods for detecting fluid infiltration at a catheter infusion site of a patient.

In some embodiments, a sensor assembly for detecting fluid infiltration at a catheter infusion site in a patient may generally include a first elongate sensor, a second elongate sensor, a first marking, and a second marking. The first elongate sensor member may be configured to couple to a patient at a first location proximate a catheter infusion site. The second elongate sensor member may be configured to couple to the patient at a second location proximate the catheter infusion site. The second elongate sensor member may comprise an envelope including an inferior elongate member and a superior elongate member. The superior elongate member may be coupled to the inferior elongate member, defining an interior space intermediate the inferior and superior elongate members. The interior space of the envelope may be configured to receive the first elongate sensor member therein, and an open end of the envelope may be configured to allow a first end of the first elongate sensor member to protrude from the open end of the envelope. The first marking may be coupled to the first elongate sensor member, and the second marking may be coupled to the superior elongate member of the second elongate sensor member. The first elongate sensor member may be slidably coupled within the second elongate sensor member such that the first and second elongate sensor members are translatable relative to each other. The first and second markings may be configured to indicate a range of relative positions between the first and second elongate sensor members as the first and second elongate sensor members translate relative to each other. At least one relative position within a range of relative positions between the first and second elongate sensor members may be indicative of infiltration at the catheter infusion site.

In some embodiments of the sensor assembly, the first marking may comprise a first shape having a first color and a first size, and the second marking may comprise a second shape having a second color and a second size.

In some embodiments of the sensor assembly, the first and second shapes and the first and second sizes may be substantially similar to each other, and the first and second colors may be different from each other. Thus, in a first position, the first marking may visually occlude the second marking and, in a second position, the first marking may not visually occlude at least a portion of the second marking in order to indicate that infiltration at the catheter infusion site has occurred.

In some embodiments, the sensor assembly may also include a light sensor configured to detect at least one of the first color and the second color.

In some embodiments of the sensor assembly, a first adhesive member may be configured to couple the first elongate sensor member to the patient at the first location proximate the catheter infusion site, and a second adhesive member may be configured to couple the inferior elongate member of the second elongate sensor member to the patient at the second location proximate the catheter infusion site.

In some embodiments of the sensor assembly, a removable inferior cover may be configured to protect the first and second adhesive members, and a removable superior cover may be configured to maintain a relative position between the first and second elongate sensor members.

In some embodiments, the sensor assembly may also an anti-stiction component configured to reduce friction between the first and second elongate sensor members.

In some embodiments, a sensor for detecting infiltration at catheter infusion site may include a first elongate sensor member configured to couple to a patient at a first location proximate a catheter infusion site, a second elongate sensor member configured to couple to the patient at a second location proximate the catheter infusion site, at least one first marking coupled to the first elongate sensor member, and at least one second marking coupled to the second elongate sensor member. The first elongate sensor member may be slidably coupled to the second elongate sensor member such that the first and second elongate sensor members are translatable relative to each other. The at least one first and second markings may be configured to indicate a range of relative positions between the first and second elongate sensor members as the first and second elongate sensor members translate relative to each other. At least one relative position within a range of relative positions between the first and second elongate sensor members may be indicative of infiltration at the catheter infusion site.

In some embodiments of the sensor, the at least one first marking may comprise a first shape having a first color and a first size, and the at least one second marking may comprise a second shape having a second color and a second size.

In some embodiments of the sensor, the first and second shapes and the first and second sizes may be substantially similar to each other, and the first and second colors may be different from each other. Thus, in a first position, the at least one first marking may visually occlude the at least one second marking and, in a second position, the at least one first marking may not visually occlude at least a portion of the at least one second marking in order to indicate that an infiltration event at the catheter infusion site has occurred.

In some embodiments of the sensor, the second elongate sensor member may comprise an envelope. The envelope may include an inferior elongate member and a superior elongate member coupled to the inferior elongate member to define an interior space between the inferior and superior elongate members. The interior space of the envelope may be configured to receive the first elongate sensor member therein. An open end of the envelope may be configured to allow a first end of the first elongate sensor member to protrude from the open end of the envelope.

In some embodiments of the sensor, a first adhesive member may be configured to couple the first elongate sensor member to the patient at the first location proximate the catheter infusion site, and a second adhesive member may be configured to couple the second elongate sensor member to the patient at the second location proximate the catheter infusion site.

In some embodiments of the sensor, a removable inferior cover may be configured to protect the first and second adhesive members, and a removable superior cover may be configured to maintain a relative position between the first and second elongate sensor members.

In some embodiments, the sensor may also include an anti-stiction component configured to reduce friction between the first and second elongate sensor members.

In some embodiments, a method for detecting fluid infiltration at a catheter infusion site of a patient with a sensor may include applying a first elongate sensor member to a first location proximate the catheter infusion site and applying a second elongate sensor member to a second location proximate the catheter infusion site. The method may also include inspecting the sensor after it has been applied to the patient to ensure that a first marking of the first elongate sensor member is occluded by a second marking of the second elongate sensor member. The method may also include monitoring the sensor to detect subsequent infiltration at the catheter infusion site of the patient. The first elongate sensor member may be slidably coupled to the second elongate sensor member such that the first and second elongate sensor members are translatable relative to each other. The first and second markings may be configured to indicate a range of relative positions between the first and second elongate sensor members as the first and second elongate sensor members translate relative to each other. At least one relative position within a range of relative positions between the first and second elongate sensor members may be indicative of infiltration at the catheter infusion site.

In some embodiments of the method, the sensor may further comprise a first adhesive member and a second adhesive member. Applying the sensor at the catheter infusion site of the patient may additionally include applying pressure to the first adhesive member to couple the first elongate sensor member to the patient at the first location and applying pressure to the second adhesive member to couple the second elongate sensor member to the patient at the second location.

In some embodiments, the method may also include removing a removable inferior cover configured to protect the first and second adhesive members of the sensor, applying the sensor to the catheter infusion site of the patient, and removing a removable superior cover from the sensor to allow the first and second elongate sensor members to translate relative to each other.

In some embodiments of the method, monitoring the sensor to detect subsequent infiltration at the catheter infusion site may include visually detecting a color associated with at least one of the first and second markings.

In some embodiments of the method, monitoring the sensor to detect subsequent infiltration at the catheter infusion site may include electronically detecting a color associated with at least one of the first and second markings via a light sensor.

In some embodiments of the method, monitoring the sensor to detect subsequent infiltration at the catheter infusion site may include measuring a distance between the first marking and the second marking.

It is to be understood that both the foregoing general description and the following detailed description are exemplary and explanatory and are not restrictive of the embodiments of the present disclosure, as claimed. It should be understood that the various embodiments of the present disclosure are not limited to the arrangements and instrumentality shown in the drawings. It should also be understood that the embodiments of the present disclosure may be combined, or that other embodiments may be utilized and that structural changes, unless so claimed, may be made without departing from the spirit or scope of the various embodiments of the present disclosure. The following detailed description is, therefore, not to be taken in a limiting sense.

BRIEF DESCRIPTION OF THE DRAWINGS

Example embodiments will be described and explained with additional specificity and detail through the use of the accompanying drawings in which.

It is to be understood that the Figures are for purposes of illustrating the concepts of the present disclosure and may not be drawn to scale. Furthermore, the Figures illustrate exemplary embodiments and do not represent limitations to the scope of the present disclosure.

DESCRIPTION OF EMBODIMENTS

Exemplary embodiments of the present disclosure will be best understood by reference to the Figures, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and systems, as represented in the Figures, is not intended to limit the scope of the present disclosure, as claimed in this or any other application claiming priority to this application, but is merely representative of exemplary embodiments of the present disclosure.

Figure 1:
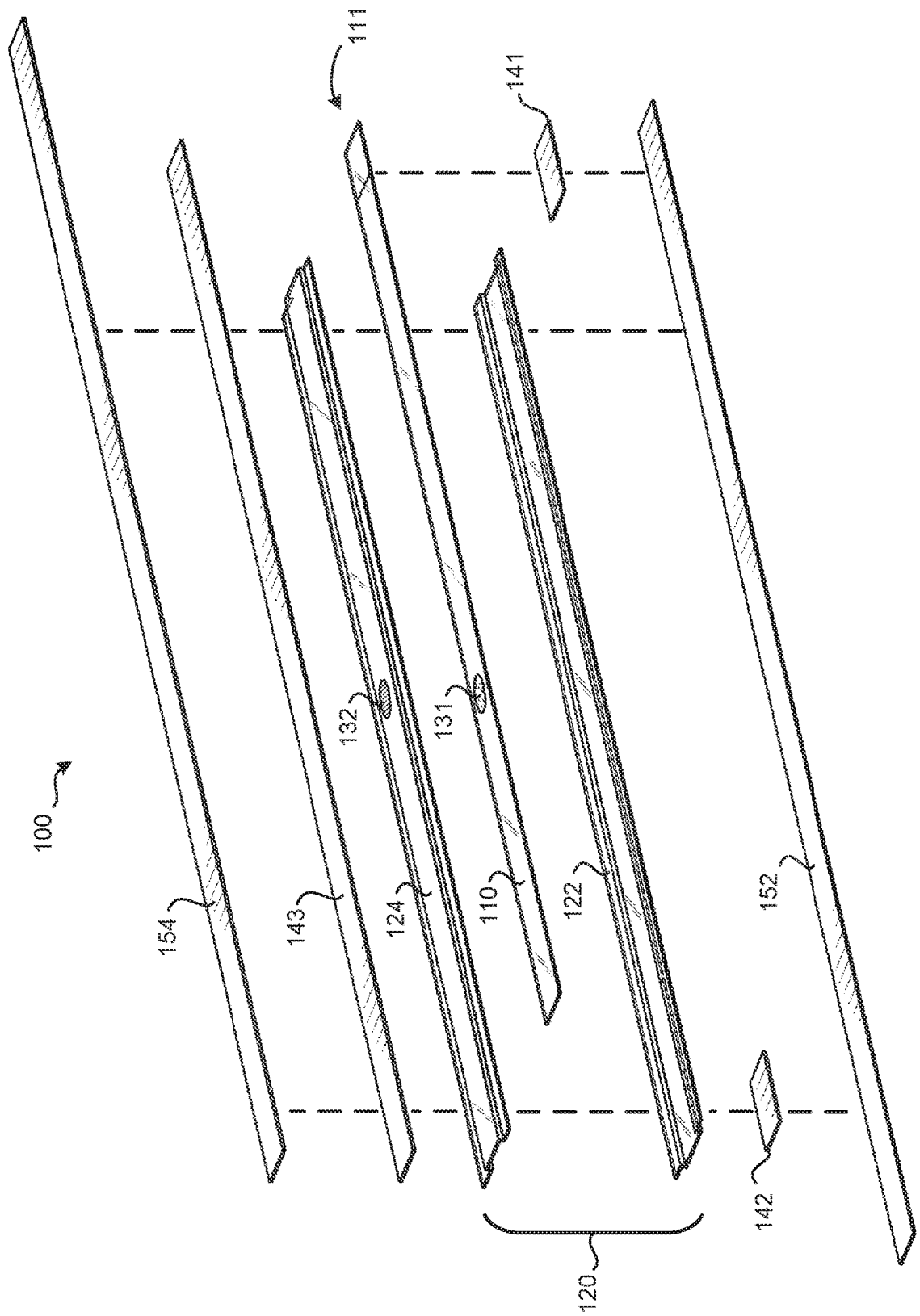
FIG. 1 is an exploded view of a sensor configured to detect fluid infiltration at a catheter infusion site of a patient, according to some embodiments.
Figure 2:
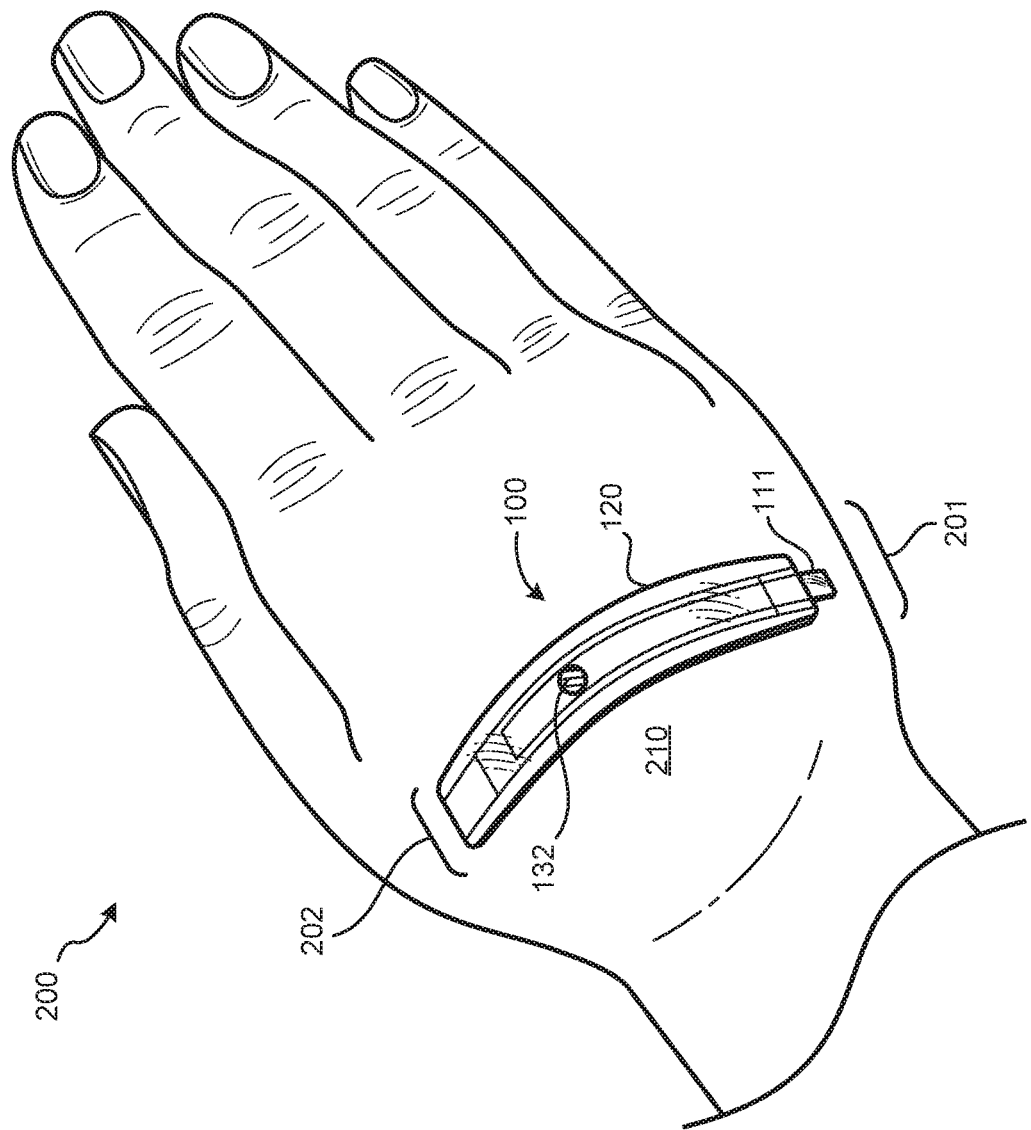
FIG. 2 illustrates the sensor of FIG. 1 assembled together and applied proximate a catheter infusion site of a patient before an infiltration event has occurred.
Figure 3:
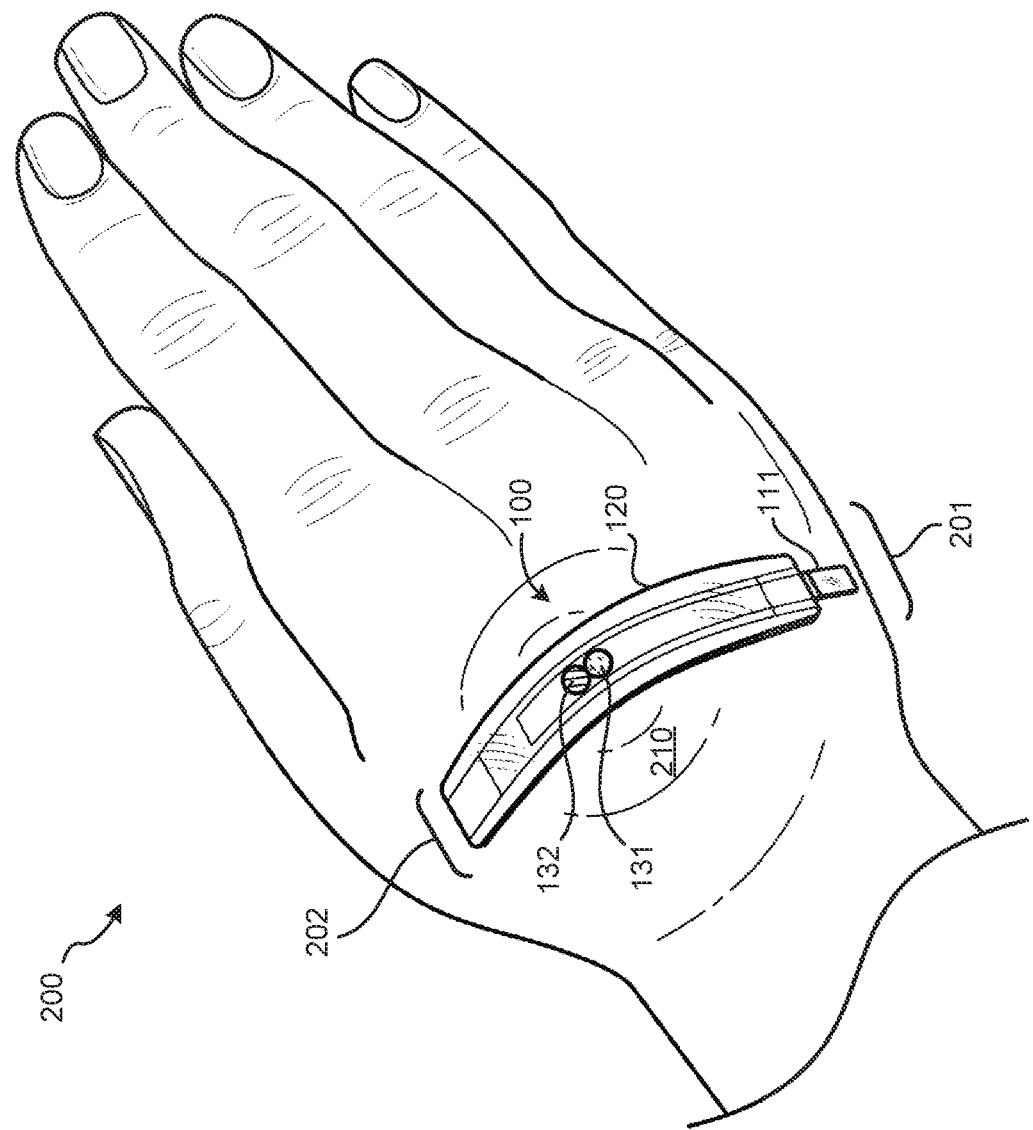
FIG. 3 illustrates the sensor of FIG. 2 after an infiltration event has occurred.

FIGS. 1-3 illustrate various views of a sensor assembly (or sensor 100) for detecting fluid infiltration at a catheter infusion site 210 of a patient, according to some embodiments. Specifically, FIG. 1 illustrates an exploded view of the sensor 100; FIG. 2 illustrates the sensor 100 assembled together and coupled to the patient proximate the catheter infusion site 210 before an infiltration event has occurred at the catheter infusion site 210; and FIG. 3 illustrates the sensor 100 after an infiltration event has occurred at the catheter infusion site 210. For example, note how the patient's hand 200 is shown as slightly enlarged or "bulging" out in FIG. 3 due to fluid infiltrating into the patient's hand 200. When this occurs, a surface distance between two fixed points on the patient's hand 200 will increase proximate the catheter infusion site. The sensor(s) disclosed herein are designed to sense and indicate an increase in such surface distances. The catheter infusion site 210 on the patient (e.g., on the hand 200 of the patient), was merely chosen as one example catheter infusion site on a patient for purposes of illustration only in the present disclosure. Accordingly, it will be understood that any of the sensor(s) and/or method(s) described herein may be utilized at any desired catheter infusion site on a patient.

In general, the sensor 100 may include a first elongate sensor member 110, a second elongate sensor member 120, a first marking 131, and a second marking 132.

In some embodiments, the first elongate sensor member 110 may be configured to couple to the patient at a first location 201 proximate the catheter infusion site 210 (e.g., see FIGS. 2 and 3). A first adhesive member 141 may be utilized to couple the first elongate sensor member 110 to the patient at the first location 201 proximate the catheter infusion site 210, in at least one embodiment. Likewise, the second elongate sensor member 120 may be configured to couple to the patient at a second location 202 proximate the catheter infusion site 210. A second adhesive member 142 may be utilized to couple the second elongate sensor member 120 to the patient at the second location 202 proximate the catheter infusion site 210, in at least one embodiment. Any of the adhesive members described herein in may be double-sided adhesive members and/or single-sided adhesive members.

In some embodiments, the second elongate sensor member 120 may comprise an envelope. The envelope may comprise an inferior elongate member 122 and a superior elongate member 124. The inferior elongate member 122 and the superior elongate member 124 may be coupled to each other along their lengths in order to define an interior space intermediate the inferior and superior elongate members 122, 124. The interior space intermediate the inferior and superior elongate members 122, 124 may be configured to slidably receive the first elongate sensor member 110 therein. However, one (or both) of the distal ends of the inferior and superior elongate members 122, 124 may not be coupled to each other in order to create one or more open ends in the envelope. In this manner, an open end of the envelope can allow a first end 111 of the first elongate sensor member 110 to protrude from the open end of the envelope.

In some embodiments, the first marking 131 may be coupled to the first elongate sensor member 110 and the second marking 132 may be coupled to the superior elongate member 124 of the second elongate sensor member 120.

In some embodiments, at least one of the first marking 131 and the second marking may comprise a plurality of markings.

In some embodiments, the first marking may comprise a first shape (e.g., a circle, a square, etc.) having a first color (e.g., red, black, etc.) and a first size, and the second marking may comprise a second shape (e.g., a circle, a square, etc.) having a second color (e.g., red, black, etc.) and a second size.

In some embodiments, the first and second shapes and the first and second sizes may be substantially similar to each other, and the first and second colors may be different from each other (e.g., the first marking may be a red circle and the second marking may be a black circle having a substantially similar size, in one non-limiting example).

In some embodiments, the first elongate sensor member 110 may be slidably coupled within the second elongate sensor member 120 such that the first and second elongate sensor members 110, 120 are translatable relative to each other. The first and second markings 131, 132 may be configured to indicate a range of relative positions between the first and second elongate sensor members 110, 120 as the first and second elongate sensor members 110, 120 translate relative to each other. At least one relative position within a range of relative positions between the first and second elongate sensor members 110, 120 may be indicative of infiltration at the catheter infusion site. For example, in a first position of the sensor 100 (e.g., before an infiltration event has occurred), the first marking 131 may be visually occluded by the second marking 132 positioned directly above the first marking 131 (e.g., see FIG. 2). However, in a second position of the sensor 100 (e.g., after an infiltration event has occurred), the second marking 132 may not visually occlude at least a portion of the first marking 131 to indicate that an infiltration event at the catheter infusion site 210 has occurred (e.g., see FIG. 3).

In some embodiments, detection of an infiltration event may be accomplished by visually detecting a color (or a color change) associated with at least one of the first and second markings 131, 132.

In some embodiments, detection of an infiltration event may be accomplished by electronically detecting a color (or a color change) associated with at least one of the first and second markings 131, 132. This may be accomplished with an LED and/or a light sensor (not shown). A signal generated by the light sensor may then be used to trigger an alarm via any known method in the art (e.g., via a blue tooth signal to a phone, via an electronic signal to a pump to stop further catheter infusion, etc.).

In some embodiments, detection of an infiltration event may be accomplished by measuring a distance between the first marking 131 and the second marking 132 either visually or electronically (e.g., via a linear encoder, not shown).

In summary, there are any number of different ways to detect and/or measure translation between the first and second elongate sensor members 110, 120 to identify when an infiltration event has occurred, and each of these methods are contemplated and incorporated herein in accordance with the spirit and scope of the present disclosure.

In some embodiments, the sensor 100 may also include a removable inferior cover 152. The removable inferior cover 152 may be configured to protect the first and second adhesive members 141, 142 during storage and transportation of the sensor 100 prior to use. In this manner, a clinician may remove the removable inferior cover 152 from the sensor 100 and immediately couple the sensor 100 to the patient at the catheter infusion to help maximize the "stickiness" of the first and second adhesive members 141, 142.

In some embodiments, the sensor 100 may also include a removable superior cover 154 and/or a third adhesive member 143. The removable superior cover 154 and/or the third adhesive member 143 may be configured to maintain a relative position between the first and second elongate sensor members 110, 120 during storage and transportation of the sensor 100 prior to use. For example, as the sensor 100 is manufactured and assembled, the first marking 131 may be positioned directly below the second marking 132 (e.g., at a first or "starting" position for the sensor 100) and then the third adhesive member 143 and/or the removable superior cover 154 may be applied to the sensor 100 to maintain this first/starting position during storage and transportation of the sensor 100 prior to use. In this manner, a clinician may remove the removable inferior cover 152 from the sensor 100, apply the sensor to the catheter infusion site of the patient, and then remove the removable superior cover 154 (and/or a third adhesive member 143) from the sensor 100 in order to allow the first and second elongate sensor members 110, 120 to translate relative to each other after the sensor has been coupled to the patient. The sensor 100 is then free to expand and begin the process of monitoring the catheter infusion site for a possible infiltration event.

In some embodiments, the sensor 100 may also include an anti-stiction component (not shown). The anti-stiction component may be configured to reduce friction between the first and second elongate sensor members 110, 120 to ensure that the first and second elongate sensor members 110, 120 are free to translate relative to each other. Example anti-stiction components may include, but are not limited to: (1) dimples, depressions, bumps, patterns, etc., formed on one or both of the first and second elongate sensor members 110, 120 in order to reduce stiction; (2) a lubricant applied to one or both of the first and second elongate sensor members 110, 120 in order to reduce stiction; (3) one or more materials incorporated into one or both of the first and second elongate sensor members 110, 120 in order to reduce stiction, etc.

In some embodiments, at least some of the components of the sensor 100 may be made from a flexible clear plastic material in order to facilitate conformance of the sensor 100 to the catheter infusion site 210, and/or to facilitate visual detection of the first marking 131 through the second elongate sensor member 120. However, it will be understood that any of the components of the sensor 100 may be made any suitable material.

Figure 4:
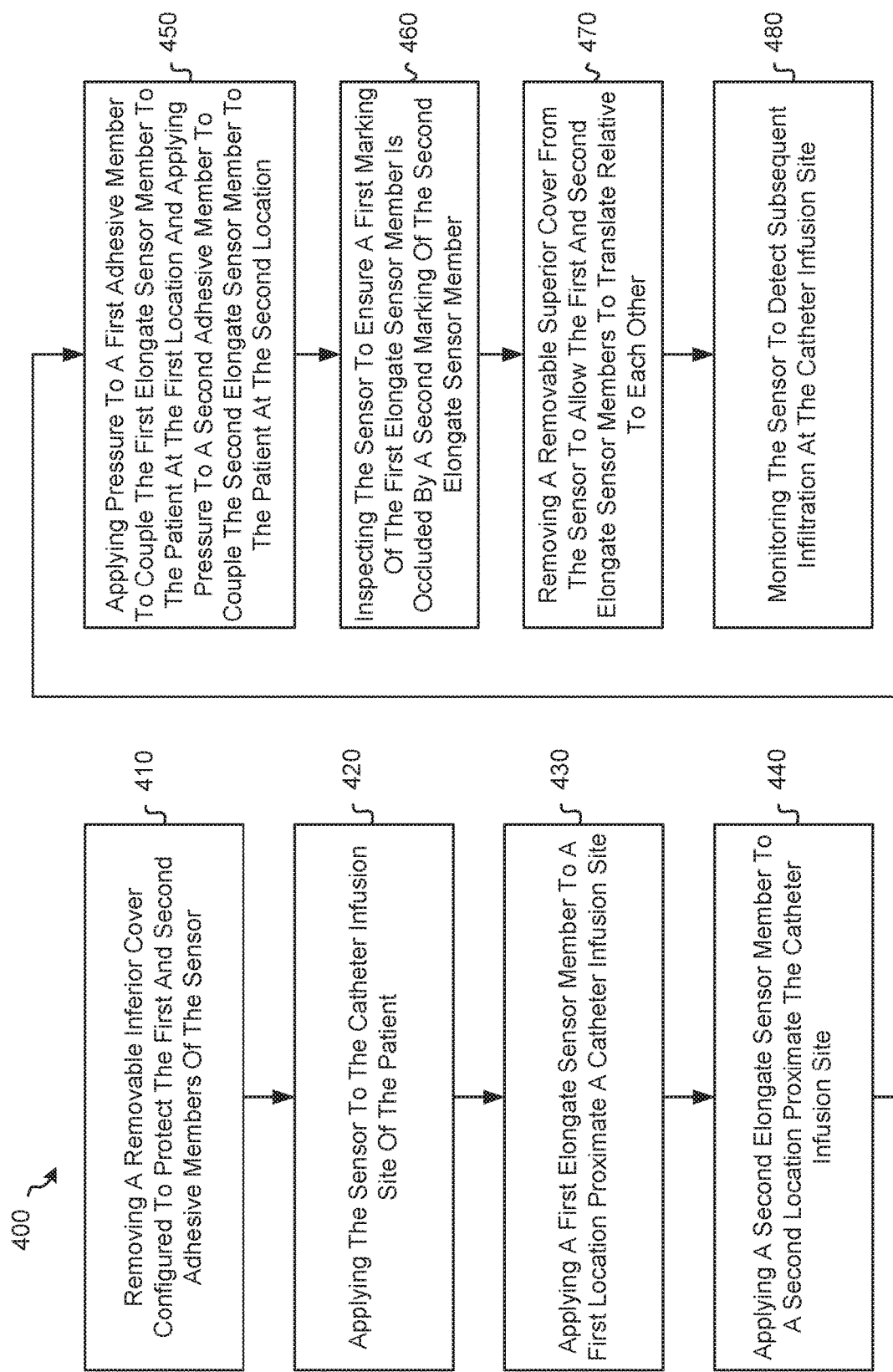
FIG. 4 is a flow chart of a method for detecting fluid infiltration at a catheter infusion site of a patient.

FIG. 4 illustrates a flow chart of a method 400 for detecting fluid infiltration at a catheter infusion site of a patient with a sensor. The method 400 may begin with a step 410 in which a removable inferior cover may be removed from the sensor. In some embodiments, the removable inferior cover may be configured to protect a first adhesive member and a second adhesive member of the sensor.

Once the removable inferior cover has been removed from the sensor, the method 400 may proceed to a step 420 in which the sensor may be applied to the catheter infusion site of the patient.

In some embodiments, the sensor may be applied to the catheter infusion site of the patient by applying a first elongate sensor member to a first location proximate the catheter infusion site (in a step 430) and applying a second elongate sensor member to a second location proximate the catheter infusion site (in a step 440). In a particular embodiment, the sensor may be applied to the catheter infusion site of the patient by applying pressure to a first adhesive member in order to couple the first elongate sensor member to the patient at the first location and applying pressure to a second adhesive member in order to couple the second elongate sensor member to the patient at the second location (in a step 450).

Once the sensor has been applied to the catheter infusion site of the patient, the method 400 may proceed to a step 460 in which the sensor may be inspected (after it has been applied to the patient) to ensure that a first marking of the first elongate sensor member is occluded by a second marking of the second elongate sensor member. This may be referred to as a "first position" or a "starting position," which may indicate that an infiltration event has not yet occurred at the catheter infusion site.

Once the sensor has been inspected to ensure that the first marking of the first elongate sensor member is occluded by the second marking of the second elongate sensor member, the method 400 may proceed to a step 470 in which a removable superior cover may be removed from the sensor to allow the first and second elongate sensor members to translate relative to each other.

Once the removable superior cover has been removed from the sensor to allow the first and second elongate sensor members to translate relative to each other, the method 400 may proceed to a step 480 in which the sensor may be monitored to detect subsequent infiltration at the catheter infusion site of the patient. Infiltration detection may be facilitated by the sensor, given that: (1) the first elongate sensor member may be slidably coupled to the second elongate sensor member such that the first and second elongate sensor members are translatable relative to each other; (2) the first and second markings may be configured to indicate a range of relative positions between the first and second elongate sensor members as the first and second elongate sensor members translate relative to each other; and (3) at least one relative position within a range of relative positions between the first and second elongate sensor members may be indicative of infiltration at the catheter infusion site.

Any methods disclosed herein comprise one or more steps or actions for performing the described method. One or more of the method steps and/or actions may be omitted from any of the methods disclosed herein. Moreover, any of the method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. It is to be understood that any of the embodiments of the present disclosure, or any portion(s) of any of the embodiments of the present disclosure, may be combined together in any number of different ways.

Similarly, it should be appreciated that in the above description of embodiments, various features are sometimes grouped together in a single embodiment, Figure, or description thereof for the purpose of streamlining the disclosure. This disclosure format, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Description Of Embodiments are hereby expressly incorporated into this Description Of Embodiments, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the Figures, the Figures are not necessarily drawn to scale unless specifically indicated.

As defined herein, "substantially equal to" means "equal to," or within about a + or − 10% relative variance from one another.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the apparatus and systems disclosed herein.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

I claim:

1. A sensor assembly for detecting fluid infiltration at a catheter infusion site in a patient, the sensor assembly comprising:
   a first elongate sensor member configured to couple to a patient at a first location proximate a catheter infusion site;
   a second elongate sensor member configured to couple to the patient at a second location proximate the catheter infusion site, the second elongate sensor member comprising an envelope, the envelope comprising:
      an inferior elongate member; and
      a superior elongate member coupled to the inferior elongate member and defining an interior space intermediate the inferior and superior elongate members,
   wherein:
      the interior space of the envelope is configured to receive the first elongate sensor member therein; and
      an open end of the envelope is configured to allow a first end of the first elongate sensor member to protrude from the open end of the envelope;
   a first marking coupled to the first elongate sensor member; and
   a second marking coupled to the superior elongate member of the second elongate sensor member;
   wherein:
      the first elongate sensor member is slidably coupled within the second elongate sensor member such that the first and second elongate sensor members are translatable relative to each other, wherein the first elongate sensor member is configured to translate with respect to the second elongate sensor member in response to infiltration at the catheter infusion site;

the first and second markings are configured to indicate a range of relative positions between the first and second elongate sensor members as the first and second elongate sensor members translate relative to each other; and at least one relative position within a range of relative positions between the first and second elongate sensor members is indicative of infiltration at the catheter infusion site.

2. The sensor assembly of claim 1, wherein:
the first marking comprises a first shape having a first color and a first size; and
the second marking comprises a second shape having a second color and a second size.

3. The sensor assembly of claim 2, wherein:
the first and second shapes and the first and second sizes are substantially similar to each other; and
the first and second colors are different from each other; wherein:
   in a first position, the second marking visually occludes the first marking; and
   in a second position, the second marking does not visually occlude at least a portion of the first marking to indicate infiltration at the catheter infusion site.

4. The sensor assembly of claim 2, further comprising a light sensor configured to detect at least one of the first color and the second color.

5. The sensor assembly of claim 1, further comprising:
a first adhesive member configured to couple the first elongate sensor member to the patient at the first location proximate the catheter infusion site; and
a second adhesive member configured to couple the inferior elongate member of the second elongate sensor member to the patient at the second location proximate the catheter infusion site.

6. The sensor assembly of claim 5, further comprising:
a removable inferior cover configured to protect the first and second adhesive members; and
a removable superior cover configured to maintain a relative position between the first and second elongate sensor members.

7. The sensor assembly of claim 1, further comprising an anti-stiction component configured to reduce friction between the first and second elongate sensor members.

8. A sensor for detecting infiltration at catheter infusion site comprising:
a first elongate sensor member configured to couple to a patient at a first location proximate a catheter infusion site;
a second elongate sensor member configured to couple to the patient at a second location proximate the catheter infusion site;
at least one first marking coupled to the first elongate sensor member; and
at least one second marking coupled to the second elongate sensor member;
wherein:
   the first elongate sensor member is slidably coupled to the second elongate sensor member such that the first and second elongate sensor members are translatable relative to each other, wherein the first elongate sensor member is configured to translate with respect to the second elongate sensor member in response to infiltration at the catheter infusion site;
   the at least one first and second markings are configured to indicate a range of relative positions between the first and second elongate sensor members as the first and second elongate sensor members translate relative to each other; and
   at least one relative position within a range of relative positions between the first and second elongate sensor members is indicative of infiltration at the catheter infusion site.

9. The sensor of claim 8, wherein:
the at least one first marking comprises a first shape having a first color and a first size; and
the at least one second marking comprises a second shape having a second color and a second size.

10. The sensor of claim 9, wherein:
the first and second shapes and the first and second sizes are substantially similar to each other; and
the first and second colors are different from each other; wherein:
   in a first position, the at least one second marking visually occludes the at least one first marking; and
   in a second position, the at least one second marking does not visually occlude at least a portion of the at least one first marking to indicate infiltration at the catheter infusion site.

11. The sensor of claim 8, wherein:
the second elongate sensor member comprises an envelope, the envelope comprising:
an inferior elongate member; and
a superior elongate member coupled to the inferior elongate member and defining an interior space between the inferior and superior elongate members, wherein:
   the interior space of the envelope is configured to receive the first elongate sensor member therein; and
   an open end of the envelope is configured to allow a first end of the first elongate sensor member to protrude from the open end of the envelope.

12. The sensor of claim 11, further comprising:
a first adhesive member configured to couple the first elongate sensor member to the patient at the first location proximate the catheter infusion site; and
a second adhesive member configured to couple the second elongate sensor member to the patient at the second location proximate the catheter infusion site.

13. The sensor of claim 12, further comprising:
a removable inferior cover configured to protect the first and second adhesive members; and
a removable superior cover configured to maintain a relative position between the first and second elongate sensor members.

14. The sensor of claim 8, further comprising an anti-stiction component configured to reduce friction between the first and second elongate sensor members.

* * * * *